US 6,955,692 B2

(12) United States Patent
Grundei

(10) Patent No.: US 6,955,692 B2
(45) Date of Patent: Oct. 18, 2005

(54) LEG PROSTHESIS

(75) Inventor: Hans Grundei, Lübeck (DE)

(73) Assignee: ESKA Implants GmbH & Co., Lübeck (DE)

(*) Notice: Subject to any disclaimer, the term of this patent is extended or adjusted under 35 U.S.C. 154(b) by 0 days.

(21) Appl. No.: 10/778,383

(22) Filed: Feb. 13, 2004

(65) Prior Publication Data

US 2004/0193286 A1 Sep. 30, 2004

(30) Foreign Application Priority Data

Feb. 17, 2003 (DE) .......................................... 103 07 328

(51) Int. Cl.$^7$ ................................................ A61F 2/74
(52) U.S. Cl. .......................................... 623/40; 623/45
(58) Field of Search ................................ 623/27, 40–46

(56) References Cited

U.S. PATENT DOCUMENTS

| 2,568,053 | A | * | 9/1951 | Catranis ........................ 623/26 |
| 5,443,524 | A | * | 8/1995 | Sawamura et al. ............ 623/24 |
| 5,571,205 | A | * | 11/1996 | James ........................... 623/24 |
| 6,425,925 | B1 | * | 7/2002 | Grundei ........................ 623/32 |
| 6,451,061 | B1 | * | 9/2002 | Grunei .......................... 623/40 |

FOREIGN PATENT DOCUMENTS

| DE | 197 54 690 A1 | 7/1999 |
| DE | 198 59 931 A1 | 7/2000 |
| DE | 199 53 972 A1 | 6/2001 |
| EP | 0 358 056 B1 | 10/1993 |
| EP | 0 549 855 B1 | 3/1996 |

OTHER PUBLICATIONS

Dietl H. et al., "The Application of Electronics in Prosthetics for Lower Extremities," Med. Orth. Tech. 117:31–35 (1997).

* cited by examiner

Primary Examiner—Bruce E Snow
(74) Attorney, Agent, or Firm—Akin Gump Strauss Hauer & Feld, LLP

(57) ABSTRACT

A leg prosthesis adapted to a thigh stump includes an adapter (2) for a knee joint (3), a knee joint (3) mounted on this adapter, and a prosthetic lower leg (4) coupled to the knee joint (3). A prosthetic foot (5) is attached to this prosthetic lower leg and can pivot into a toes-raised foot position. The knee joint (3) upon transition from the extended position to the bent position performs a combined rolling-sliding movement about a pivot axis (6). A force-transmitting element (8) moves the prosthetic foot (5) substantially from the toes-down foot position to the toes-raised foot position during bending of the knee joint (3). Each bending position of the knee joint is transformed by a converter into an unambiguous electrical signal, which is supplied to a programmable control device, which generates a signal used to control an electrically adjustable actuator, which increases or decreases the resistance of the knee joint against or for further bending according to the signal.

9 Claims, 3 Drawing Sheets

LEG PROSTHESIS

BACKGROUND OF THE INVENTION

The present invention is directed to a leg prosthesis for adapting to a thigh stump, as known from German published patent application DE-A-199 53 972. It comprises an adapter for a knee joint, which adapter is anchored in the femur stump of the patient with a post. At the distal end the adapter emerges from the thigh stump and there it can be coupled to an artificial knee joint, as known, for example, from European Patent EP-B-0 358 056.

A prosthetic lower leg, which in turn carries an attached prosthetic foot at its distal end, is coupled to the knee joint. This prosthetic foot can pivot from a pointed (toes-down) foot position to a cocked (toes-raised) foot position.

The knee joint according to the proposal of European Patent EP-B-0 358 056 is formed such that for the transition from the extended position to the bent position, it carries out a combined rolling and sliding motion about a pivot axis. In contrast to a pure hinge joint, the knee joint of this generic type of leg prosthesis is formed such that the distance of a point of the knee joint lying in front of the pivot axis, when viewed dorsally, to the end of the prosthetic lower leg continuously decreases. In other words, the distance of a point lying in front of the pivot axis, when viewed ventrally instead, to the end of the prosthetic lower leg constantly increases.

One problem for patients with a partially amputated upper leg is that, among other things, he must walk with the healthy foot in a strong toes-down foot position, in order to allow the prosthetic foot to swing through forwardly with the leg prosthesis for a new step. This is true independent of whether the prosthetic foot can pivot on the prosthetic lower leg or is rigidly attached. The necessity of bringing the healthy, natural foot into an exaggerated or extreme toes-down foot position, so that the prosthesis can swing through, causes a rather non-physiological type of motion and thus a great stress is placed on the spine while walking.

From the generic type shown in this patent, it can be gathered that between at least one support point lying in front of the pivot axis, when viewed dorsally, and/or a support point lying in front of the pivot axis, when viewed ventrally, and the prosthetic foot, a force-transmitting element is arranged which, upon bending of the knee joint, moves the prosthetic foot from a toes-down foot position or neutral foot position of the artificial foot in large measure to the toes-raised foot position. In this way, the necessity to bring the healthy, natural foot into a non-physiological toes-down foot position, so that the artificial leg can swing through, should no longer exist, and the sequence of movement should appear more natural.

Although the leg prosthesis of the generic type has already achieved clear progress relative to the basic state of the art, it does not allow the generation of a dynamic bionic gait, i.e., a gait sympathetic with nature. The reason for this is to be seen in that the swinging movement of the prosthetic lower leg is the same over wide ranges. In contrast, in a natural leg, the movement of the knee joint changes as a function of its bending position. Thus, in the bent state, i.e., in the range of about 90°, the knee can move relatively freely. With decreasing bending angle, i.e., for extension of the leg, the resistance against further bending increases. In the extended state of the leg, the knee joint is de facto rigid.

The lack of changing resistance forces against further bending of the knee thus impairs the dynamic bionic gait for the leg prosthetic of the generic type shown in this patent.

BRIEF SUMMARY OF THE INVENTION

In view of this background, the object of the present invention is to create relief for this problem, i.e., to improve a leg prosthesis of the generic type, such that a dynamic bionic gait is enabled.

This object is achieved in that each bending position of the knee joint is converted by a converter into an unambiguous electrical signal, which is supplied to a programmable control device, which generates a signal, with which an electrically adjustable actuator is controlled. This actuator increases or decreases the resistance of the knee joint against or for further bending according to the signal.

Therefore, the aforementioned resistance is controlled electronically in the leg prosthesis according to the invention. For an extended leg in the range of 160° to 180°, the resistance is set so high that the leg is de facto rigid. In the transition range between 120° and 135°, the knee is positioned in a secured state, but still allows a bending motion. In the bent state of the knee, the lower leg can move relatively freely according to natural appearance. Prerequisites for the control are the detection of the bending position of the knee joint and the unambiguous allocation of an electrical signal, with which further control is performed. The unambiguous bending position represents not only the bending angle, but also the backwards, translational movement of the upper part of the knee relative to the lower part for increasing bending of the joint. This is the peculiarity of the knee joint, as known from the above-mentioned European Patent EP-B-0 358 056. A pure pole hinge, as used in European Patent EP-B-0 549 855, is not able to exhibit these properties. A knee joint with a pure pole or hinge joint does not satisfy the condition, namely that the distance of a point lying in front of the pivot axis, when viewed dorsally, to the end of the prosthetic lower leg steadily decreases with increasing bending of the knee joint. The predetermined pole curve would likewise entail a decrease of the distance, for example, for the first movement from the extended position toward the bent position. However, after reaching a dead point, the distance would increase again. For a leg prosthesis performing the complete motion of the knee joint from the extended position to the bent position, this would lead to the foot being initially easily pivoted to the toes-raised foot position, but after passing the mentioned dead point, it would pivot back into the original position or toes-down foot position, so that as a result, at full bend of the knee joint, a quasi toes-down foot position of the foot relative to the prosthetic lower leg would exist. The generation of an unambiguous electrical signal for each bending position would thus be impossible.

According to a preferred embodiment, the force-transmitting element is constructed from a connecting rod attached to the knee joint and to the prosthetic foot. At the proximal end the connecting rod can be attached, for example, in the dorsal region of the knee joint, so that it can be used when the distance of the attachment point to the end of the prosthetic lower leg decreases for the execution of the pivoting motion of the prosthetic foot from the original position into the desired toes-raised foot position. The prosthetic foot moves especially reliably into the toes-raised foot position during the motion of the knee joint from the extended position into the bent position, if the leg prosthesis is formed according to an advantageous refinement, in which the prosthetic foot is connected to the prosthetic lower leg, so that it can pivot about a ventral pivot point and in which the force-transmitting element is attached to the prosthetic foot at a dorsal support point. The force-transmitting element then causes the introduction of a torque about the ventral pivot point, whereby the prosthetic foot reliably pivots into the toes-raised foot position.

According to an especially preferred embodiment, a flexible band is provided, which can be adjusted in its effective length and is tensioned between the prosthetic foot and a bearing on the prosthetic lower leg, wherein the slack increases upon increased bending of the knee joint.

This band essentially assumes the function of the natural Achilles tendon. The main function of the band is to return the foot to its original position in the extended position of the knee joint. The band further serves for individual setting of a toes-down foot position of the prosthetic foot, based on the adjustability of the band's effective length, for example, by a threaded stop, to which the appropriate end of the band can be screwed. This adjustment usually differs from patient to patient due to different heels.

Integrated in the force-transmitting element is preferably a restoring element, which actively brings the prosthetic foot back into its original position when the knee is extended after previously being bent. This active restoring element supports the operation of the above-mentioned band at the beginning of the movement from the bent position into the extended position of the knee. Here, the mentioned force-transmitting element starts the restoring effect first, while the band first shows its effect when approaching the extended position.

With the above-described refinement, it is preferred that the restoring element have a guiding sleeve receiving a spiral spring, as well as a plunger guided in the sleeve as part of the connecting rod, such that with increasing bending of the knee joint, the spring is increasingly compressed, and upon extension of the knee joint, the spring force pivots the prosthetic foot into the original position. Thus, the more the knee is bent, the higher the spring forces generated in the restoring element. It is advantageous for the guiding sleeve to be mounted in a housing fastened on the prosthetic upper leg. This produces a compact unit, which is relatively easy for the patient to manipulate.

It is especially preferred that the electrically adjustable actuator be constructed as a hydraulic cylinder with several adjustable valves. The mentioned electrical signal, which unambiguously represents each bending position of the knee joint and which comes from the converter, serves after further processing in the control device to control the electrically adjustable valves, which for their part influence the flow of the hydraulic fluid in the cylinder. This hydraulic control regulates the force used to move the piston of the hydraulic cylinder.

Other actuators than a hydraulic cylinder are conceivable, for example a magnetic brake. Considerably unique is that the actuator controls the resistance of the knee joint for or against further bending. The forces generated by the actuator are realized by a suitable mechanism, for example an arrangement of at least one connecting band engaging the upper part of the knee joint.

Depending on the corresponding bending position of the knee, for one thing, the foot is steadily pivoted by the force-transmitting element from the toes-down foot position to a toes-raised foot position, and each bending position is allocated to a resistance against or for further bending of the knee joint. This provides the envisioned dynamic, bionic movement sequence.

The converter, which should generate an unambiguous signal for each bending position, preferably converts the bending movement into a translational movement of a measurement block guided in guiding rails, which generates the signal representing the bending position of the knee joint in an associated sensor.

The conversion of the complicated movement of a knee joint for a bending movement, which represents a rolling and sliding movement, is not trivial. The use, for example, of a rotation potentiometer about the bending axis of the knee does not lead to the desired goal, because in the signal generated in this way, absolutely no part of the translational movement of the upper part relative to the lower part is represented for increasing backwards bending of the knee joint. The measurement block is preferably connected to at least one connecting band, with which the actuator guides the force generated by it into the knee joint.

The signal generated by the converter is supplied to the programmable control device, which generates a patient-specific signal. For each patient, a movement sequence can be programmed individually, i.e., each bending position of the knee joint can be allocated to a resistance force, which is generated by the actuator, specific to the patient. This table generated as a kind of look-up table, is determined manually, wherein, for example, the effective length of the mentioned flexible band, but also the resistance of the actuator in certain bending positions of the knee joint can be set. The values determined in this way can then be stored in the programmable control device, for example, by means of a laptop, and are then available for use.

An especially preferred configuration of the converter is such that the measurement block is a magnet and the sensor allocated to it is a Hall sensor, which is passed by the magnet, which is connected to the connecting band for transferring the actuator forces. The great advantage of this arrangement is that it is absolutely free from wear and tear.

The power supply of the control device, the actuator, and optionally the converter, can be realized by the batteries or accumulators arranged in the prosthesis.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

In the following, like parts are provided with the same reference numbers.

DETAILED DESCRIPTION OF THE INVENTION

Figure 1:
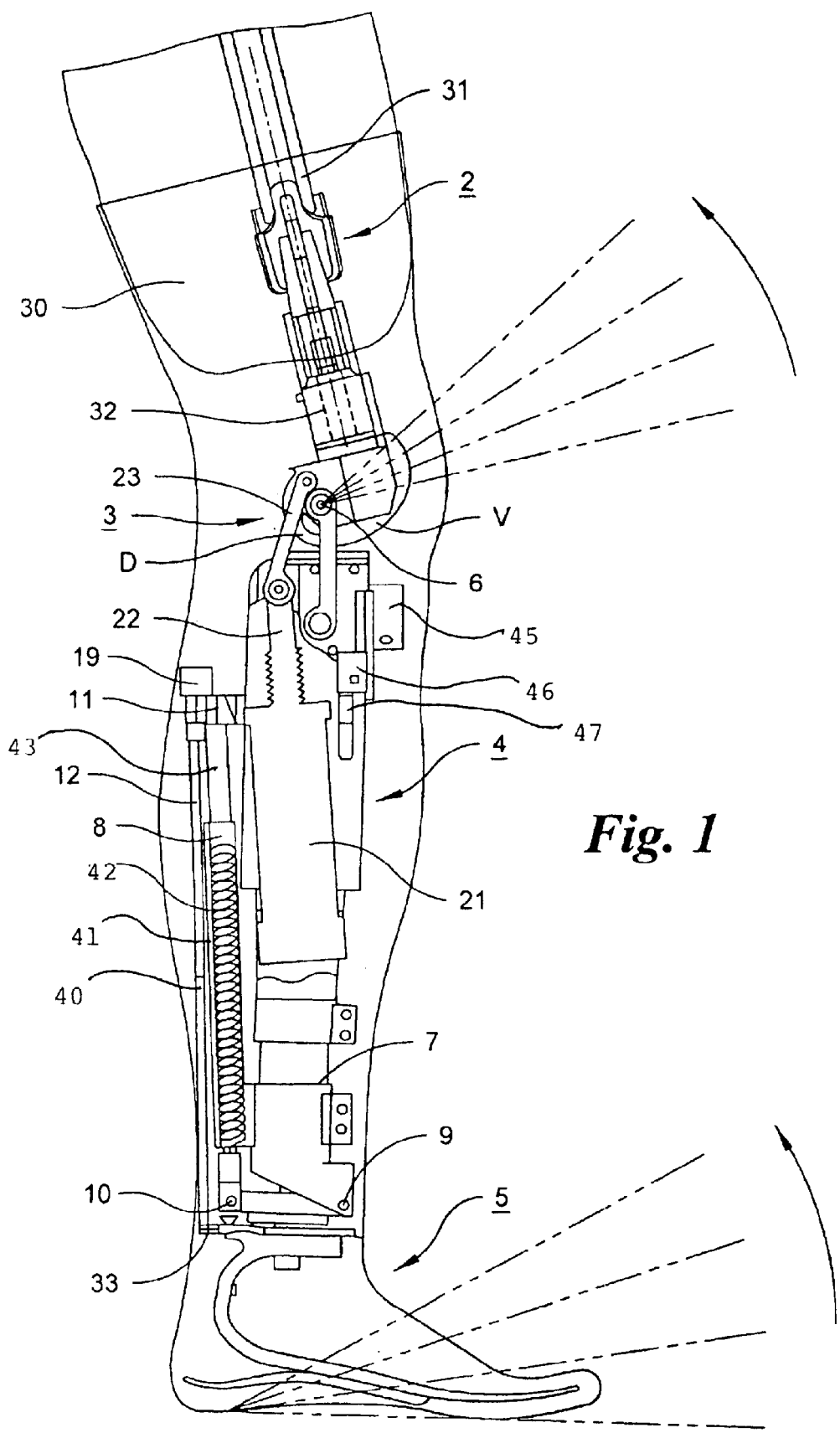
FIG. 1 is a schematic side view, broken away to shown the internal parts, of an entire leg prosthesis according to the present invention.
Figure 2:
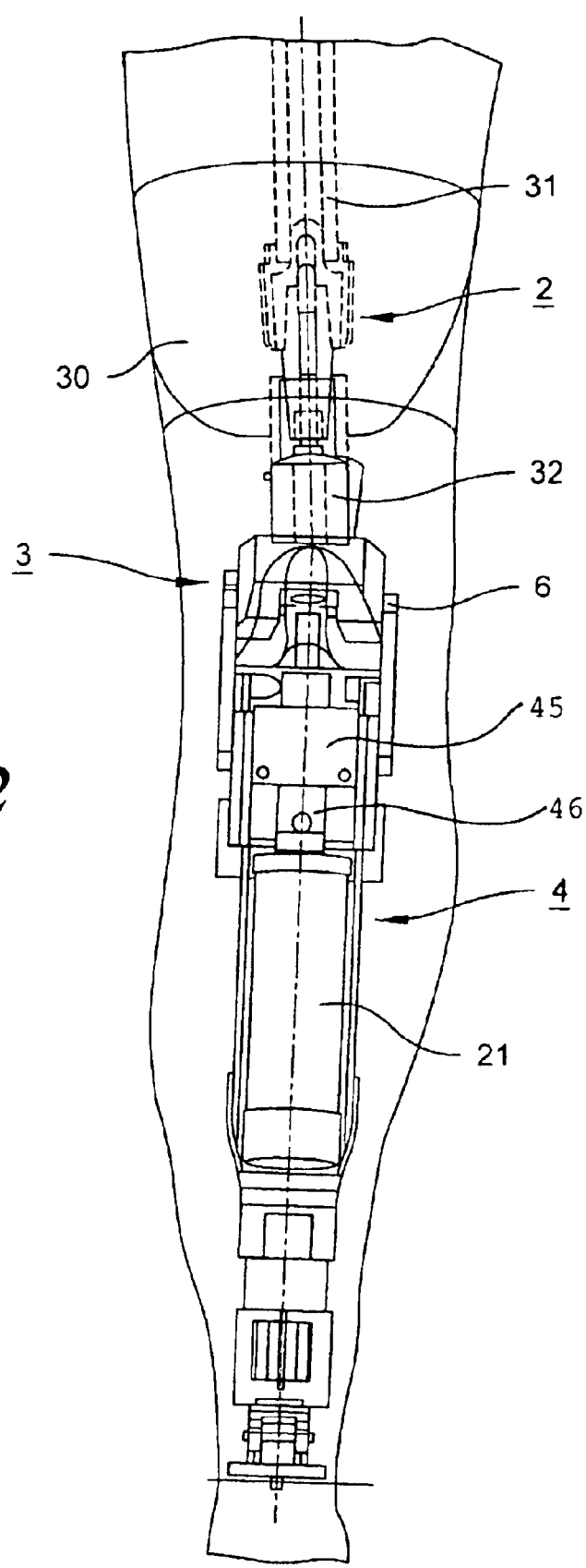
FIG. 2 is a ventral view of the prosthesis according to FIG. 1 without a foot.
Figure 3:
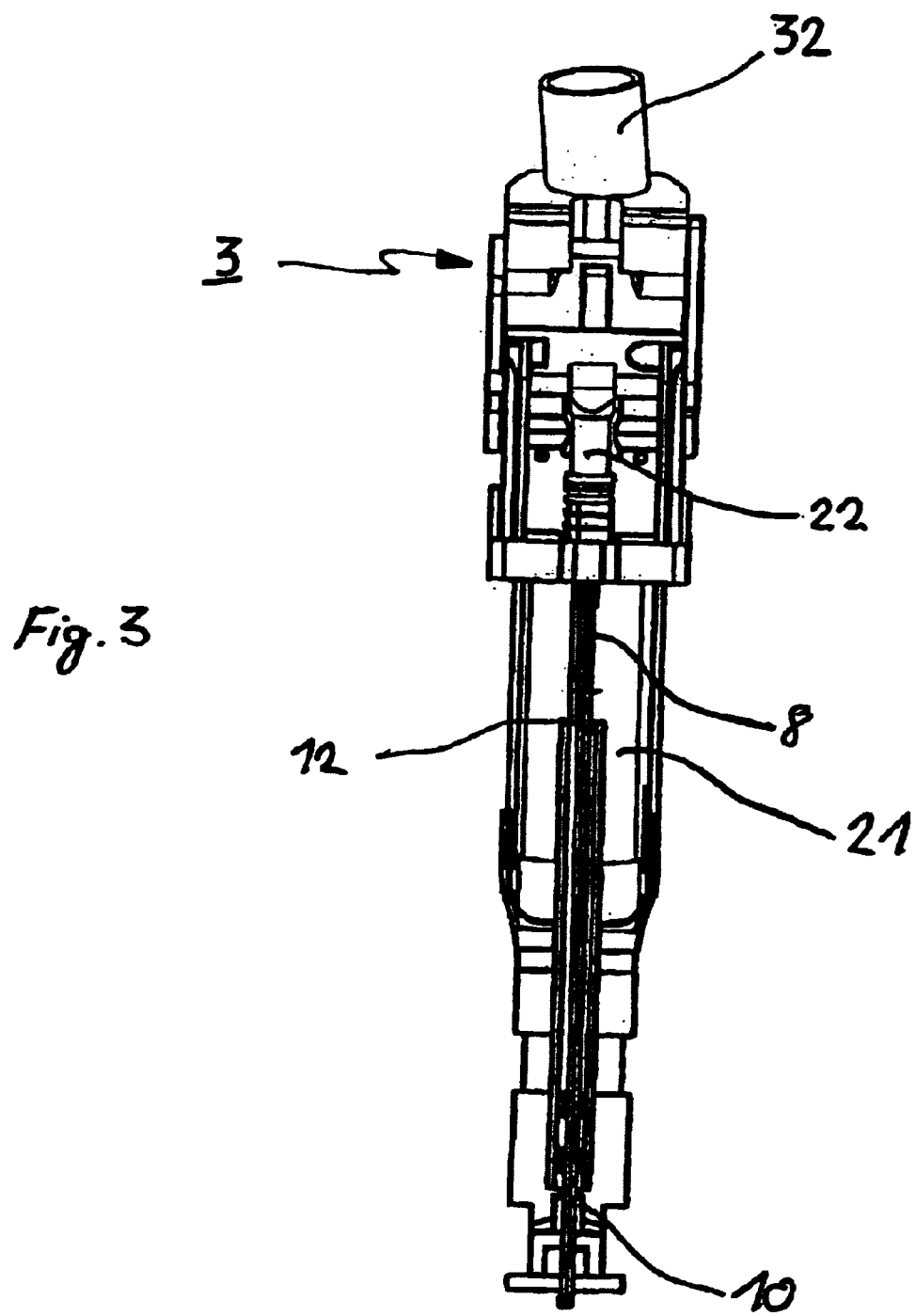
FIG. 3 is a dorsal view of the knee joint and the prosthetic lower leg mechanism of the prosthesis according to FIG. 1.

The leg prosthesis consists of an adapter 2, which is connected to the thigh stump 30 of the patient in such a manner that the adapter 2 is fixed to the femur stump 31. To the coupling element 32 of the adapter 2 a knee joint 3 is coupled, to which is connected on the distal end a prosthetic lower leg 4, which finally carries a prosthetic foot 5, in such a manner that the prosthetic foot 5 is pivotably connected to the prosthetic lower leg 4.

The knee joint 3 has a pivot axis 6, about which the upper-leg part of the knee joint 3 can pivot relative to the lower-leg part 4. The knee joint 3 has the special property that it executes a rolling-sliding movement about the pivot axis 6 during the transition from the extended position to the bending position. This leads to the fact that the distance of a point D in front of the pivot axis 6, when viewed dorsally, to the end 7 of the prosthetic lower leg 4 steadily decreases. Correspondingly, the mentioned distance for a point V in front of the pivot axis 6, when viewed ventrally, increases steadily during execution of the movement from the extended position into the bent position of the knee joint 3.

The prosthetic foot 5 is pivotably attached at the end 7 of the prosthetic lower leg 4 about a ventral pivot point 9. When the prosthetic foot 5 is pivoted about the pivot point 9, the prosthetic foot 5 moves into the toes-raised foot position. This is indicated in FIG. 1 by the series of rays in the foot region and also in the knee region. When the knee is bent in the direction of the indicated arrow, then the foot prosthesis is raised in the direction of the indicated arrow.

The coupling of the movement of the knee joint 3 with the movement of the prosthetic foot 5 is accomplished by the force-transmitting element 8, which is attached proximally at the knee joint 3. The force of the force-transmitting element 8 is introduced dorsally into the attachment piece 33 at the support point 10. The attachment piece 33 here assumes the function of the natural upper ankle joint.

In addition, for the shown embodiment, a flexible band 12 is tensioned dorsally between a support 11 fixed on the prosthetic lower leg 4 and the prosthetic foot 5. The band 12 consists, for example of a flexible steel cord. It assumes the function of the natural Achilles tendon. It serves to swing the prosthetic foot 5 completely back into the original position during transition from the bent position into the extended position of the knee joint 3. In addition, it serves for individual adjustment of a toes-raised foot position of the prosthetic foot 5. For this purpose, the band 12 has a threaded sleeve at the proximal end, which interacts with an attachment 19 with internal threads, as well as with the support 11, such that the attachment 19 forms a stop on the support 11. By turning the screw of the attachment 19, the original foot position (toes-down foot position) can be set specific to the patient.

A restoring element 40 in the force-transmitting element 8, forces the prosthetic foot 5 back into its original position during extension of the knee joint 3 after previous bending. The restoring element 40 here comprises a guiding sleeve 41, receiving a spiral spring 42 and a plunger 43 guided in the sleeve.

A hydraulic cylinder 21 with its piston rod 22 is arranged in the prosthetic lower leg 4. The hydraulic cylinder 21 serves as an actuator for adjusting the resistance of the knee joint against or for further bending. Here, the hydraulic cylinder 21 is powered by multi-chamber valves (not shown) appropriately with hydraulic fluid. The multi-chamber valves can be controlled electronically by a programmable control device. This control device receives a signal from a converter, which transforms the current bending position of the knee joint 3 into an unambiguous electrical signal. The programmable control device and converter are part of the sensor unit 45. The bending position of the knee joint 3 correspondingly generates for the hydraulic cylinder 21 an appropriate force, which is transferred via its piston rod 22.

At least one connecting band 23 is attached on the dorsal side of the knee joint 3, the other end of the connecting band being connected to the piston rod 22 of the hydraulic cylinder 21. By this at least one connecting band 23, the hydraulic cylinder 21 controls the resistance against further bending of the knee joint 3.

A measurement block 46, which is guided in guiding rails 47 and which is part of the sensor unit 45, is connected to the connecting band 23. With increasing bending of the knee joint 3, the measurement block is moved further downwards by the connecting band 23. Here, it passes a sensor in the sensor unit 45, preferably a Hall sensor, if the measurement block 46 is a magnet, whereby a signal is generated. This signal unambiguously represents the respective position of the knee joint 3 and is supplied to the already mentioned control device for further processing.

Above all, what is essential for the leg prosthesis according to the invention is not only the presence of a forced coupling between the bending of the knee joint 3 and the pivoting movement of the prosthetic foot 5, but also that the resistance of the knee joint against or for further bending increases or decreases according to the respective bending position of the knee.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A leg prosthesis for adapting to a thigh stump, comprising an adapter (2) for a knee joint (3), a knee joint (3) mounted on the adapter, a prosthetic lower leg (4) coupled to the knee joint (3), a prosthetic foot (5) coupled to the prosthetic lower leg and pivotable to a toes-raised foot position, wherein the knee joint (3) is constructed such that it performs a combined rolling-sliding motion about a pivot axis (6) during a transition from an extended position of the leg prosthesis to a bent position of the leg prosthesis, wherein a distance of a point (D) in front of the pivot axis (6), when viewed dorsally, to an end (7) of the prosthetic lower leg (4) steadily decreases with increasing bending or a distance of a point (V) in front of the pivot axis (6), when viewed ventrally, to the end (7) of the prosthetic lower leg (4) steadily increases, a force-transmitting element (8) attached between at least one support point in front of the pivot axis (6), when viewed dorsally, or one support point in front of the pivot axis (6), when viewed ventrally, and the prosthetic foot (5), wherein the force-transmitting element (8) moves the prosthetic foot (5) to a large degree from the toes-down foot position to the toes-raised foot position during bending of the knee joint (3), and a converter for transforming each bending position of the knee joint into an unambiguous electrical signal, which is supplied to a programmable control device, wherein the control device generates an actuating signal used to control an electrically adjustable actuator, which increases or decreases the resistance of the knee joint against or for further bending according to the actuating signal.

2. The leg prosthesis according to claim 1, wherein the force-transmitting element (8) is formed by a connecting rod attached to the knee joint (3) and to the prosthetic foot (5).

3. The leg prosthesis according to claim 2, wherein the prosthetic foot (5) is coupled to the prosthetic lower leg (4) such that the prosthetic foot (5) can pivot about a ventral pivot point (9) and wherein the force-transmitting element (8) is attached to the prosthetic foot (5) at a dorsal support point (10).

4. The leg prosthesis according to claim 1, further comprising a flexible band (12), adjustable in its effective length, is tensioned between the prosthetic foot (5) and a support (11) on the prosthetic lower leg (4), wherein a slack in the flexible band increases for increasing bending of the knee joint (3).

5. The leg prosthesis according to claim 2, further comprising a restoring element integrated into the force-transmitting element (8) for extension of the knee joint (3) after previous bending, wherein the restoring element brings the prosthetic foot (5) back into its original (toes-down) foot position.

6. The leg prosthesis according to claim 5, wherein the restoring element has a guiding sleeve receiving a spiral spring and a plunger guided in the sleeve as part of the connecting rod, such that for increasing bending of the knee joint (3), the spring is increasingly compressed, and for extension of the knee joint (3), the spring force pivots the prosthetic foot (5) into the original foot position.

7. The leg prosthesis according to claim 6, wherein the guiding sleeve is supported in a housing mounted on the prosthetic lower leg (4).

8. The leg prosthesis according to claim 1, wherein the converter transforms the bending movement into a translational movement of a measurement block guided in guiding rails, such that the movement of the measurement block generates in an associated sensor the unambiguous electrical signal representing the bending position of the knee joint.

9. The leg prosthesis according to claim 8, wherein the measurement block is a magnet and the sensor is a Hall sensor.

\* \* \* \* \*